United States Patent

Ando et al.

Patent Number: 5,552,424
Date of Patent: Sep. 3, 1996

[54] ISOXAZOLINES AS ANTIINFLAMMATORY AGENTS

[75] Inventors: Akemi Ando; Rodney W. Stevens, both of Handa, Japan

[73] Assignee: Pfizer Inc., New York, N.Y.

[21] Appl. No.: 432,183

[22] Filed: May 5, 1995

[30] Foreign Application Priority Data

Nov. 20, 1992 [JP] Japan ..................... 4-312259

[51] Int. Cl.$^6$ ................ A61K 31/42; C07D 261/04
[52] U.S. Cl. ............................. 514/378; 548/240
[58] Field of Search ..................... 548/240; 514/378

[56] References Cited

FOREIGN PATENT DOCUMENTS

| | | |
|---|---|---|
| 237082 | 9/1987 | European Pat. Off. . |
| 245825 | 11/1987 | European Pat. Off. . |
| 320628 | 6/1989 | European Pat. Off. . |
| 459748 | 12/1991 | European Pat. Off. . |

*Primary Examiner*—Patricia L. Morris
*Attorney, Agent, or Firm*—Peter C. Richardson; Paul H. Ginsburg; Bryan C. Zielinski

[57] ABSTRACT

Certain novel isoxazoline compounds having the ability to inhibit the 5-lipoxygenase enzyme and having formula (I),

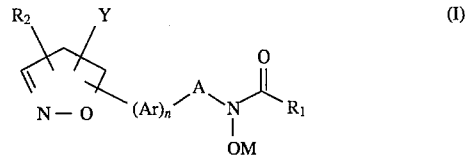

wherein $R_1$ is $C_1$–$C_4$ alkyl or —$NR_3R_4$; $R_3$ and $R_4$ are each independently H or $C_1$–$C_4$ alkyl; M is H or a pharmaceutically acceptable cation; A is $C_1$–$C_6$ alkylene, $C_2$–$C_6$ alkenylene or $C_2$–$C_6$ alkynylene; Ar is phenylene or mono-, di- or tri-substituted phenylene wherein the substituents are each independently selected from halogen, $C_1$–$C_4$ alkyl and $C_1$–$C_4$ alkoxy; n is an integer of 0 or 1; Y is H or $C_1$–$C_4$ alkyl; $R_2$ is $C_1$–$C_{10}$ alkyl, $C_1$–$C_4$ arylalkyl or $C_2$–$C_4$ arylalkenyl; and said aryl and each aryl moiety in said arylalkyl and arylalkenyl may be substituted by from one to three substituents independently selected from halogen, $C_1$–$C_6$ alkyl, $C_1$–$C_6$ alkoxy, halosubstituted $C_1$–$C_4$ alkyl, halosubstituted $C_1$–$C_4$ alkoxy, aryl-$C_1$–$C_4$ alkoxy, phenoxy and mono-, di- and tri-substituted phenoxy wherein the substituents are each independently selected from halogen, $C_1$–$C_4$ alkyl, $C_1$–$C_4$ alkoxy and halosubstituted $C_1$–$C_4$ alkyl. These compounds are useful in the treatment or alleviation of inflammatory diseases, allergy and cardiovascular diseases in mammals and as the active ingredient in pharmaceutical compositions for treating such conditions.

19 Claims, No Drawings

ISOXAZOLINES AS ANTIINFLAMMATORY AGENTS

BACKGROUND OF THE INVENTION

This invention relates to novel N-hydroxyurea and hydroxamic acid derivatives. The compounds of the present invention inhibit the action of the enzyme lipoxygenase and are useful in the treatment or alleviation of inflammatory diseases, allergy and cardiovascular diseases in mammals, especially human subjects. This invention also relates to pharmaceutical compositions comprising such compounds.

Arachidonic acid is known to be the biological precursor of several groups of biologically active endogenous metabolites. The first step in the metabolism of arachidonic acid is its release from membrane phospholipids, via the action of phospholipase A2. Arachidonic acid is then metabolized either by cyclooxygenase to produce prostaglandins including prostacyclin, and thromboxanes or by lipoxygenase to generate hydroperoxy fatty acids which may be further converted to the leukotrienes. The leukotrienes are extremely potent substances which elicit a wide variety of biological responses, often in the nanomolar to picomolar concentration range. The peptidoleukotrienes ($LTC_4$, $LTD_4$, $LTE_4$) are important bronchoconstrictors and vasoconstrictors, and also cause plasma extravasation by increasing capillary permeability. $LTB_4$ is a potent chemotactic agent, enhancing the influx of leukocytes and inducing their subsequent degranulation at the site of inflammation. A pathophysiological role for leukotrienes has been implicated in a number of human disease states including asthma, rheumatoid arthritis, gout, psoriasis, adult respiratory distress syndrome, inflammatory bowel diseases (e.g. Crohn's disease), endotoxin shock, and ischemia-induced myocardial injury. Any agent that inhibits the action of lipoxygenases is expected to be of considerable therapeutic value for the treatment of acute and chronic inflammatory conditions.

Among the compounds of similar structure to the object compounds of the present invention are those disclosed in EP 459748 A2 and WO 89/04299.

SUMMARY OF THE INVENTION

The present inventors have worked to prepare compounds capable of inhibiting the action of lipoxygenase and after extensive research they have succeeded in synthesizing a series of compounds disclosed in detail herein.

The present invention provides novel N-hydroxyurea and hydroxamic acid derivatives of the following chemical formula I:

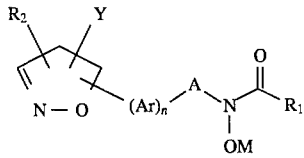

wherein $R_1$ is alkyl having 1 to 4 carbon atoms or $-NR_3R_4$; $R_3$ and $R_4$ are each independently hydrogen or alkyl having 1 to 4 carbon atoms; M is hydrogen or a pharmaceutically acceptable cation; A is alkylene having 1 to 6 carbon atoms, alkenylene having 2 to 6 carbon atoms or alkynylene having 2 to 6 carbon atoms; Ar is phenylene or mono-, di- or tri-substituted phenylene wherein the substituents are each independently selected from halogen, alkyl having 1 to 4 carbon atoms and alkoxy having 1 to 4 carbon atoms; n is an integer of 0 or 1; Y is hydrogen or alkyl having 1 to 4 carbon atoms; $R_2$ is alkyl having 1 to 10 carbon atoms, arylalkyl having 1 to 4 carbon atoms in the alkyl moiety, arylalkenyl having 2 to 4 carbon atoms in the alkenyl moiety or aryl; and said aryl and each aryl moiety in said arylalkyl and arylalkenyl may be optionally substituted with one to three substituents which are each independently selected from halogen, alkyl having 1 to 6 carbon atoms, alkoxy having 1 to 6 carbon atoms, halosubstituted alkyl having 1 to 4 carbon atoms, halosubstituted alkoxy having 1 to 4 carbon atoms, arylalkoxy having 1 to 4 carbon atoms in the alkoxy moiety, phenoxy and mono-, di- and tri-substituted phenoxy wherein the substituents are each independently selected from halogen, alkyl having 1 to 4 carbon atoms, alkoxy having 1 to 4 carbon atoms and halosubstituted alkyl having 1 to 4 carbon atoms.

A preferred class of compounds of the invention are those of formula I, wherein $R_1$ is $NH_2$, M is hydrogen, A is $-CH(CH_3)-$, n is 0, Y is hydrogen and $R_2$ is phenyl or substituted phenyl. Within this preferred group, particularly preferred individual compounds are:
N-(1-[4,5-dihydro-3-(3-phenoxyphenyl)isoxazol-5-yl]ethyl)-N-hydroxyurea; and
N-[1-(3-[4,5-dihydro-3-(4-fluorophenyl)isoxazol-5-yl]phenyl)ethyl]-N-hydroxyurea.

Other preferred individual compounds of the invention are:
N-[4-(3-[4,5-dihydro-3-(4-fluorophenyl)isoxazol-5-yl]phenyl)-3-butyn-2-yl]-N-hyroxyurea; and
N-(3-[3-(4,5-dihydro-5-phenylisoxazol-3-yl)phenyl]-2-propyn-1-yl)-N-hydroxy-N'-methylurea.

DETAILED DESCRIPTION OF THE INVENTION

In this specification, the following definitions are used.

"Halogen" means a radical derived from the elements fluorine, chlorine, bromine and iodine.

"Alkyl" means a straight or branched hydrocarbon chain radical, including, for example, methyl, ethyl, n-propyl, isopropyl, n-butyl and the like.

"Alkoxy" means the group $-OR_5$, wherein $R_5$ is alkyl as defined above, including, for example, methoxy, ethoxy, propoxy, isopropoxy, n-butoxy and the like.

"Alkenyl" means a straight or branched hydrocarbon chain radical having one double bond including, for example, ethenyl, 1- and 2-propenyl, 2-methyl-1-propenyl, 1- and 2-butenyl and the like.

"Alkylene" means a straight or branched hydrocarbon chain spacer radical including, for example, $-CH_2-$, $-CH(CH_3)-$, $-CH_2CH_2-$, $-CH_2CH(CH_3)-$ and the like.

"Alkenylene" means a straight or branched hydrocarbon chain spacer radical having one double bond including, for example, $-CH=CH-$, $-CH=CHCH_2-$, $-CH=CHCH(CH_3)-$ and the like.

"Alkynylene" means a straight or branched hydrocarbon chain spacer radical having one triple bond including, for example, $-C\equiv C-$, $-C\equiv CCH_2-$, $-C\equiv CCH(CH_3)-$ and the like.

"Halosubstituted alkyl" means an alkyl radical as described above substituted with one or more halogens including, for example, chloromethyl, bromoethyl, trifluoromethyl and the like.

"Halosubstituted alkoxy" means an alkoxy radical as described above substituted with one or more halogens including, for example, chloromethoxy, bromoethoxy, difluoromethoxy, trifluoromethoxy and the like.

"Aryl" means an aromatic radical including, for example, phenyl, naphthyl and the like.

"Arylalkyl" means an alkyl radical which is substituted by an aryl group including, for example, benzyl, phenethyl, phenylpropyl, naphthylmethyl and the like.

"Arylalkenyl" means an alkenyl radical which is substituted by an aryl group including, for example, phenylethenyl, phenylpropenyl, naphthylethenyl and the like.

"Arylalkoxy" means an alkoxy radical which is substituted by an aryl group including, for example, benzyloxy, phenethyloxy, phenylpropoxy, naphthylmethoxy and the like.

"Pharmaceutically acceptable cation" means a non-toxic cation based on alkaline and alkaline earth metals such as sodium, lithium, potassium, calcium, magnesium and the like, as well as those based on non-toxic ammoniums, quaternary ammoniums and amine cations, including, for example, ammonium, tetramethylammonium, ethylammonium, diethylammonium, tetraethylammonium, methylamine, dimethylamine, trimethylamine, ethylamine and the like.

The compounds of formula I may be prepared by a number of synthetic methods. In the following formulae, Q is

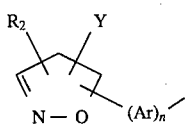

and $R_2$, Y, Ar and n are as previously defined. Although in Schemes 1 and 2, $R_1$ is $NH_2$ and methyl, respectively, other compounds of formula I wherein $R_1$ is as previously defined may be prepared in a similar manner.

In one embodiment, compounds of the formula III are prepared according to the reaction steps outlined in Scheme 1.

SCHEME 1

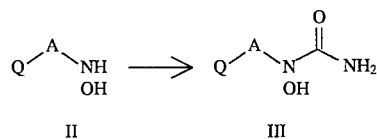

In this step the hydroxylamine II is treated with trimethylsilyl isocyanate (TMS-NCO) in a reaction-inert solvent usually at ambient through to reflux temperature. Suitable solvents which do not react with reactants and/or products are, for example, tetrahydrofuran (THF), dioxane, methylene chloride ($CH_2Cl_2$) or benzene. An alternative procedure employs treatment of II with gaseous hydrogen chloride in a reaction-inert solvent such as benzene or toluene and then subsequent treatment with phosgene. Reaction temperatures are usually in the range of ambient temperature through to boiling point of solvent. The intermediate carbamoyl chloride is not isolated but subjected to (i.e. in situ) reaction with aqueous ammonia. The product of formula III thus obtained is isolated by standard methods and purification can be achieved by conventional means, such as recrystallization and chromatography.

In another embodiment, compounds of the formula V are prepared as illustrated in Scheme 2:

SCHEME 2

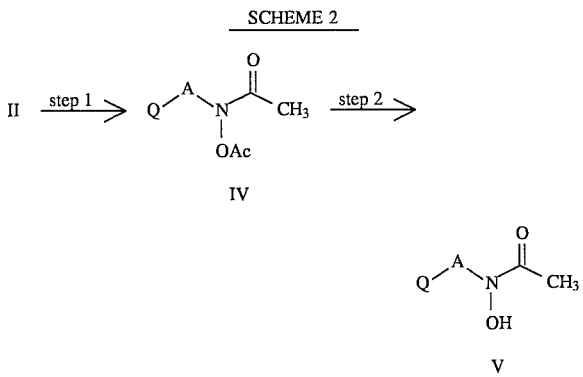

In the first step the diacetyl compound IV is prepared by standard methods known in the art. For example, the hydroxylamine II is reacted with acetyl chloride or acetic anhydride in a reaction-inert solvent in the presence of a suitable base. Preferred basic agents are triethylamine and pyridine, however sodium hydride can be utilized. Suitable reaction-inert solvents include $CH_2Cl_2$, chloroform, THF, benzene and toluene. The reaction is usually carried out in the temperature range of 0° C. through to ambient temperature. Reaction times of from 30 minutes to a few hours are common. The product can be isolated and purified by conventional procedures, such as recrystallization or chromatography.

The second step involves selective hydrolysis of IV with an appropriate base. The basic agents suitably employed in this reaction include ammonium hydroxide, sodium hydroxide, potassium hydroxide and lithium hydroxide preferably in methanol, ethanol, isopropyl alcohol or water, though binary solvent systems such as alcohol-water, THF-water and the like may be employed. Reaction temperature is usually in the range of −10° C. through to ambient temperature and the reaction is usually completed within a few minutes to several hours. The product of formula V is isolated by standard methods and purification can be achieved by conventional means, such as recrystallization and chromatography.

The aforementioned hydroxylamine II may be readily prepared by standard synthetic procedures from the corresponding carbonyl compound, i.e. ketone or aldehyde. For example, the appropriate carbonyl compound is converted to its oxime and then reduced to the requisite hydroxylamine II with a suitable reducing agent. For example, see R. F. Borch et al, *J. Am. Chem. Soc.*, 93, 2897 (1971). Reducing agents of choice include, for example, sodium cyanoborohydride and borane complexes such as borane-pyridine, borane-triethylamine and borane-dimethylsulfide, however triethylsilane in trifluoroacetic acid (TFA) may also be employed.

Alternately, hydroxylamine II can easily be prepared by treating the corresponding alcohol with N,O-bis(tert-butyloxycarbonyl)hydroxylamine under Mitsunobu-type reaction conditions followed by acid catalyzed hydrolysis (for example, employing TFA) of the N,O-protected intermediate product. It is also noteworthy that N,O-di-acetylhydroxylamine can be used in place of N,O-bis(tert-butyloxycarbonyl)hydroxylamine, thus providing a convenient route to product of formula V.

The aforementioned hydroxylamine II may also be prepared from a suitable halide compound by reaction with O-protected hydroxylamine and subsequent deprotection. See, for example, W. P. Jackson et al, *J. Med. Chem.*, 31, 499

(1988). Preferred O-protected hydroxylamines include, for example, O-tetrahydropyranyl-, O-trimethylsilyl- and O-benzylhydroxylamine.

In the case that n is 1 and the carbon chain A in the above formula is alkynylene, the corresponding hydroxylamine intermediate II may be also prepared from a suitable aryl halide compound (e.g. a bromoaryl derivative or the like) or a triflate derivative, and a corresponding N,O-protected alkynylhydroxylamine (e.g. N,O-bis(tert-butoxycarbonyl)-N-(3-butyn-2-yl)hydroxylamine or the like) by a coupling reaction with a suitable palladium catalyst (e.g. $Pd(PPh_3)_4$, $Pd(PPh_3)_2Cl_2$ or the like) and subsequent deprotection. Alternatively the corresponding hydroxylamine intermediate may be prepared from the corresponding alkynyl alcohol as described above. The alkynyl alcohol may be prepared by from a suitable aryl halide compound (e.g. a bromoaryl derivative or the like) or triflate derivative, and a corresponding alkynyl alcohol (e.g. but-3-yn-2-ol or the like) by a coupling reaction with a suitable palladium catalyst (e.g. $Pd(PPh_3)_4$, $Pd(PPh_3)_2Cl_2$ or the like).

In the case that n is 1 and the carbon chain A in the above formula is alkenylene, the corresponding hydroxylamine intermediate II may be also prepared from a suitable aryl halide compound (e.g. a bromoaryl derivative or the like) or triflate derivative, and a corresponding N,O-protected alkenylhydroxylamine (e.g. N,O-bis(tert-butoxycarbonyl)-N-(3-buten-2-yl)hydroxylamine or the like) by a coupling reaction with a suitable palladium catalyst (e.g. $Pd(PPh_3)_4$, $Pd(PPh_3)_2Cl_2$ or the like) and subsequent deprotection. Alternatively the corresponding hydroxylamine intermediate may be prepared from the corresponding alkenyl alcohol as described herein above. The alkenyl alcohol may be prepared by from a suitable alkynyl alcohol by reduction. For example, partial hydrogenation employing $Pd/BaSO_4$ catalyst or by reduction with sodium bis(2-methoxyethoxy)aluminum hydride and the like.

The hydroxylamine of formula II thus obtained by the above-mentioned representative procedures is isolated by standard methods and purification can be achieved by conventional means, such as recrystallization and chromatography.

Certain compounds described herein contain one or more asymmetric centers and may thus give rise to isomers, such as diastereomers and optical isomers. The present invention contemplates all such possible isomers as well as mixtures thereof.

The pharmaceutical compositions of the present invention comprise a compound of formula I as an active ingredient and a pharmaceutically acceptable carrier, and optionally other NSAID (non-steroidal antiinflammatory drug).

The term "pharmaceutically acceptable salts" refers to salts prepared from compounds of the present invention and non-toxic bases including inorganic bases and organic bases.

These salts can be prepared in situ during the final isolation and purification of the compounds or by separately reacting the purified compound in its free acid form with a suitable base such as the above-mentioned pharmaceutically acceptable cation.

The compounds of this invention inhibit the activity of the enzyme lipoxygenase. This inhibition can be demonstrated by standard procedures. For example, it can be demonstrated by an assay using rat peritoneal cavity resident cells, which determines the effect of said compounds on the metabolism of arachidonic acid, using the general method described in *Jap. J. Inflammation*, 7, 145–50 (1987), "Synthesis of leukotrienes by peritoneal macrophages." In this test some preferred compounds indicated low $IC_{50}$ values, in the range of 0.1 to 30 μM, with respect to lipoxygenase inhibiting activity.

In addition, the ability of the compounds of formula I to inhibit the lipoxygenase enzyme can be demonstrated in vitro using heparinized human whole blood, according to the general method described in *British J. Pharmacol.*, 99, 113–8 (1990). This method determines the inhibitory effect on 5-lipoxygenase (LO) metabolism of arachidonic acid.

The ability of the compounds of the present invention to inhibit lipoxygenase makes them useful for controlling the symptoms induced by the endogenous metabolites arising from arachidonic acid in a mammalian subject. The compounds are therefore valuable in the prevention and treatment of such disease states in which the accumulation of arachidonic acid metabolites are the causative factor; e.g. allergic bronchial asthma, skin disorders, rheumatoid arthritis, osteoarthritis and thrombosis.

The compounds of the present invention are of particular use in the treatment or alleviation of inflammatory diseases in a human subject.

For treatment of the various conditions described above, the compounds of formula I can be administered to a human subject either alone, or preferably in combination with pharmaceutically acceptable carriers or diluents in a pharmaceutical composition according to standard pharmaceutical practice.

The compounds can be administered by various conventional routes of administration including oral, parenteral and by inhalation. When the compounds are administered orally, the dose range will be from about 0.1 to 20 mg/kg per body weight of the subject to be treated per day, preferably from about 0.1 to 1.0 mg/kg per day in single or divided doses. If parenteral administration is desired, then an effective dose will be from about 0.1 to 1.0 mg/kg per body weight of the subject to be treated per day. In some instances it may be necessary to use dosages outside these limits, since the dosages will necessarily vary according to the age, weight and response of the individual patient as well as the severity of the patient's symptoms and the potency of the particular compound being administered.

For oral administration, the compounds of the formula I can be administered, for example, in the form of tablets, powders, lozenges, syrups, capsules, aqueous solutions or suspensions. In the case of tablets for oral use, carriers which are commonly used include lactose and corn starch. Lubricating agents such as magnesium stearate are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solute should be controlled to make the preparation isotonic.

EXAMPLES

The present invention is illustrated by the following examples. However, it should be understood that the invention is not limited to the specific details of these examples. Proton nuclear magnetic resonance (NMR) spectra were measured at 270 MHz unless otherwise indicated and peak positions are expressed in parts per million (ppm) downfield from tetramethylsilane. The peak shapes are denoted as follows: s-singlet, d-doublet, t-triplet, m-multiplet and br-broad.

Examples 1 & 2

N-1-(5-[3-(4-benzyloxyphenyl)-4,5-dihydroisoxazolyl])ethyl-N-hydroxyurea (two diastereomers)

Step 1, 4-benzyloxybenzaldehyde (1)

The title compound (1) was prepared from 4-hydroxybenzaldehyde according to the procedure of T. G. C. Bird et al, *J. Med. Chem.*, 34, 2176 (1991).

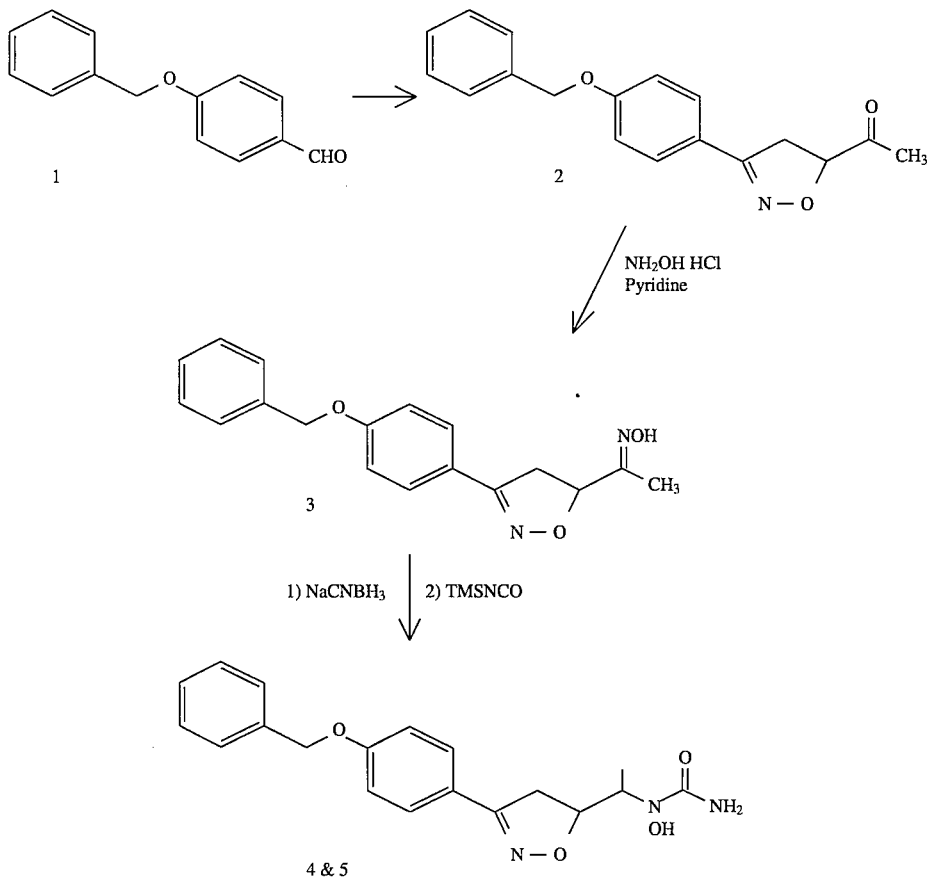

Step 2, 5-acetyl-3-(4-benzyloxyphenyl)-4,5-dihydroisoxazole (2)

The title compound (2) was prepared from the product of Step 1, above (1), according to the procedure of D. P. Curran et al, *J. Chem. Soc.* (Perkin Transaction 1), 2163 (1991).

Step 3, 1-(5-[3-(4-benzyloxyphenyl)-4,5-dihydroisoxazolyl])-1-hydroxyiminoethane (3)

To a solution of the product of Step 2, above (2, 7.80 g, 30 mmol) in pyridine (50 ml) was added hydroxylamine hydrochloride (3.20 g, 45 mmol). The mixture was stirred for 2 hours at room temperature, then the solvent was removed under reduced pressure. The residue was partitioned between ethyl acetate (100 ml) and water (50 ml) and the organic layer was washed with aqueous 6N HCl (50 ml), saturated aqueous $NaHCO_3$ (50 ml) and brine (50 ml), then was dried ($MgSO_4$) and concentrated under reduced pressure to afford the title compound (3, 6.0 g, 64% yield) as yellow solids.

$^1$H NMR ($CDCl_3$) δ: 7.63 (m, 2H), 7.41–7.25 (m, 6H), 7.01–6.98 (m, 2H), 5.24–5.17 (m, 1H), 5.11 (s, 2H), 3.45 (d, J=9.53 Hz, 2H), 1.95 (s, 3H).

Step 4, N-1-(5-[3-(4-benzyloxyphenyl)-4,5-dihydroisoxazolyl])ethyl-N-hydroxyurea (4 & 5)

To a solution of oxime product of Step 3, above (3, 5.50 g, 17 mmol) in acetic acid (25 ml) was added $NaCNBH_3$ (1.19 g, 17 mmol) portionwise in solid form. After stirring for 2 hours, the reaction mixture was poured carefully into ice cold saturated aqueous $NaHCO_3$ (100 ml) and was extracted with ethyl acetate (3×100 ml). The combined extracts were washed with water (100 ml) and brine (100 ml), dried ($MgSO_4$) and concentrated under reduced pressure to give 5.50 g of crude 1-(5-[3-(4-benzyloxyphenyl)-4,5-dihydroisoxazolyl])ethyl-1-hydroxylamine.

To a stirred solution of the hydroxylamine in THF (50 ml) was added TMS-NCO (85%, 4.5 ml, 33 mmol), and the reaction mixture was stirred at room temperature for 1.5 hours. Methanol (15 ml) was added and the reaction mixture was stirred a further 10 minutes and the solvent was removed under reduced pressure. The residue was recrystallized from methanol/THF to give one diastereomer of the title compound (4, 1.1 g, 17% yield) as colorless solids, m.p. 196.6°–198.2° C.

IR (KBr): 3500, 3300, 3200–3000, 1650, 1450, 1250, 1000, 920 $cm^{-1}$.

$^1$H NMR (DMSO-$d_6$) δ: 9.10 (s, 1H), 7.59 (d, J=8.79 Hz, 2H), 7.47–7.33 (m, 5H), 7.08 (d, J=8.80 Hz, 2H), 6.28 (s, 2H), 5.16 (s, 2H), 4.66–4.59 (m, 1H), 4.29–4.24 (m, 1H), 3.40–3.30 (m, 1H), 3.23–3.13 (m, 1H), 1.03 (d, J=6.60 Hz, 3H).

The mother liquor was concentrated under reduced pressure and the residue was recrystallized from methanol/THF to give the other diastereomer of the title compound (5, 2.37 g, 38% yield) as colorless solids, m.p. 188.9°–190.0° C.

IR (KBr): 3380, 3150, 2900, 1660, 1610, 1450, 1250, 1030, 940 cm$^{-1}$.

$^1$H NMR (DMSO-d$_6$) δ: 9.14 (s, 1H), 7.58 (d, J=8.80 Hz, 2H), 7.47–7.33 (m, 5H), 7.08 (d, J=8.79 Hz, 2H), 6.40 (s, 2H), 5.16 (s, 2H), 4.62–4.53 (m, 1H), 4.01–3.95 (m, 1H), 3.41 (dd, J=10.62, 17.21 Hz, 1H), 3.14 (dd, J=6.23, 17.22 Hz, 1H), 1.12 (d, J=6.59 Hz, 3H).

The compounds of the following Examples (3 to 15) were synthesized in the same manner used for the preparation of Examples 1 and 2. It should be noted that each pair of examples (3 and 4, 5 and 6, 7 and 8, 9 and 10, 11 and 12) consists of two diastereomers (syn-isomer and anti-isomer).

Example 3

N-[1-(4,5-dihydro-3-phenylisoxazol-5-yl)ethyl]-N-hydroxyurea m.p. 159.2°–160.7° C.

IR (KBr): 3450, 1650, 1580, 1360, 1180, 990 cm$^{-1}$.

$^1$H NMR (DMSO-d$_6$) δ: 9.02 (s, 1H), 7.63 (m, 2H), 7.40–7.38 (m, 3H), 5.67 (br s, 2H), 4.78 (m, 1H), 4.27 (m, 1H), 3.41 (dd, J=10.62, 16.86 Hz, 1H), 3.31 (dd, J=7.33, 17.22 Hz, 1H), 1.31 (d, J=6.60 Hz, 3H).

Example 4

N-[1-(4,5-dihydro-3-phenylisoxazol-5-yl)ethyl]-N-hydroxyurea m.p. 165.2'–166.9° C.

IR (KBr): 3500, 3400, 1650, 1450, 1360, 1170, 910 cm$^{-1}$.

$^1$H NMR (DMSO-d$_6$) δ: 8.92 (s, 1H), 7.65 (m, 2H), 7.39 (m, 3H), 5.53 (br s, 2H), 4.85 (dd, J=8.06, 16.86 Hz, 1H), 4.52 (m, 1H), 3.39 (dd, J=10.63, 16.86 Hz, 1H), 3.21 (dd, J=8.79, 16.79 Hz, 1H), 1.23 (d, J=6.59 Hz, 3H).

Example 5

N-(1-[4,5-dihydro-3-(4-phenoxyphenyl)isoxazol-5-yl]ethyl)-N-hydroxyurea m.p. 183.7°–185.0° C.

IR (KBr): 3500, 3400, 3150, 1660, 1420, 1260, 900 cm$^{-1}$.

$^1$H NMR (DMSO-d$_6$) δ: 9.16 (s, 1H), 7.66 (d, J=8.79 Hz, 2H), 7.43 (t, J=8.69 Hz, 2H), 7.20 (m, 1H), 7.17–7.03 (m, 4H), 6.41 (br s, 2H), 4.61 (m, 1H), 4.00 (m, 1H), 3.44 (dd, J=10.62, 17.21 Hz, 1H), 3.17 (dd, J=6.59, 17.22 Hz, 1H), 1.13 (d, J=6.23 Hz, 3H).

Example 6

N-(1-[4,5-dihydro-3-(4-phenoxyphenyl)isoxazol-5-yl]ethyl)-N-hydroxyurea m.p. 160.0°–162.2° C.

IR (KBr): 3350, 3150, 2850, 1660, 1590, 1510, 1350, 1160, 920 cm$^{-1}$.

$^1$H NMR (DSMO-d$_6$) δ: 9.15 (s, 0.34H), 9.11 (s, 0.66H), 7.66 (m, 2H), 7.43 (t, J=8.03 Hz, 2H), 7.19 (m, 1H), 7.09–7.03 (m, 4H), 6.39 (s, 0.68H), 6.27 (s, 1.32H), 4.73–4.59 (m, 1H), 4.29 (m, 0.66H), 3.99 (m, 0.34H), 3.48–3.36 (m, 1H), 3.29–3.12 (m, 1H), 1.14 (d, J=6.22 Hz, 1H), 1.04 (d, J=6.59 Hz, 2H).

Example 7

N-(1-[4,5-dihydro-3-(4-fluorophenyl)isoxazol-5-yl]ethyl)-N-hydroxyurea m.p. 159.6°–160.9° C.

IR (KBr): 3500, 3400, 3100, 2850, 1650, 1510, 1350, 1230, 920, 840 cm$^{-1}$.

$^1$H NMR (DSMO-d$_6$) δ: 9.10 (br s, 1H), 7.74–7.68 (m, 2H), 7.32–7.25 (m, 2H), 6.26 (br s, 2H), 4.70 (m, 1H), 4.29 (m, 1H), 3.43 (dd, J=10.62, 17.22 Hz, 1H), 3.22 (dd, J=8.80, 17.22 Hz, 1H), 1.04 (d, J=6.96 Hz, 3H).

Example 8

N-(1-[4,5-dihydro-3-(4-fluorophenyl)isoxazol-5-yl]ethyl)-N-hydroxyurea m.p. 154.6°–156.5° C.

IR (KBr): 3400, 3250, 1640, 1520, 1240, 1020, 920 cm$^{-1}$.

$^1$H NMR (DSMO-d$_6$) δ: 9.15 (s, 1H), 7.27–7.67 (m, 2H), 7.32–7.25 (m, 2H), 6.39 (s, 2H), 4.63 (m, 1H), 4.00 (m, 1H), 3.45 (dd, J=10.63, 17.26 Hz, 1H), 3.18 (dd, J=6.60, 17.22 Hz, 1H), 1.13 (d, J=6.59 Hz, 3H).

Example 9

N-(1-[4,5-dihydro-3-(4-trifluoromethylphenyl)isoxazol-5-yl]ethyl)-N-hydroxyurea m.p. 162.4°–163.6° C.

IR (KBr): 3500, 3350, 3150, 2850, 1630, 1480, 1320, 1180, 1120, 1070, 920 cm$^{-1}$.

$^1$H NMR (DSMO-d$_6$) δ: 9.17 (s, 1H), 7.88–7.79 (m, 4H), 6.41 (s, 2H), 4.69 (m, 1H), 4.04 (m, 1H), 3.51 (dd, J=10.63, 17.22 Hz, 1H), 3.23 (dd, J=6.96, 17.22 Hz, 1H), 1.13 (d, J=6.3 Hz, 3H).

Example 10

N-(1-[4,5-dihydro-3-(4-trifluoromethylphenyl)isoxazol-5-yl]ethyl)-N-hydroxyurea m.p. 147.5°–149.3° C.

IR (KBr): 3500, 3330, 3280, 1620, 1580, 1330, 1170, 910 cm$^{-1}$.

$^1$H NMR (DSMO-d$_6$) δ: 9.13 (s, 1H), 7.89–7.80 (m, 4H), 6.30 (s, 2H), 4.81–4.71 (m, 1H), 4.34–4.28 (m, 1H), 3.48 (dd, J=10.62, 17.22 Hz, 1H), 3.29–3.23 (m, 1H), 1.05 (d, J=6.60 Hz, 3H).

Example 11

N-(1-[4,5-dihydro-3-(4-iso-propylphenyl)isoxazol-5-yl]ethyl)-N-hydroxyurea m.p. 146.9°–149.6° C.

IR (KBr): 3500, 3350, 3300, 2950, 1600, 1570, 1450, 900 cm$^{-1}$.

$^1$H NMR (DSMO-d$_6$) δ: 9.15 (s, 0.66H), 9.11 (s, 0.34H), 7.59–7.54 (m, 2H), 7.33–7.30 (m, 2H), 6.39 (s, 1.32H), 6.28 (s, 0.68H), 4.69–4.55 (m, 1H), 4.31–4.25 (m, 1H), 4.02–3.97 (m, 1H), 3.47–3.12 (m, 1H), 2.97–2.86 (m, 1H), 1.22–1.12 (m, 7.8H), 1.04 (d, J=6.59 Hz, 1.2H).

Example 12

N-(1-[4,5-dihydro-3-(4-isopropylphenyl)isoxazol-5-yl]ethyl)-N-hydroxyurea m.p. 145.4°–146.9° C.

IR (KBr): 3500, 3400, 3250, 2950, 1650, 1580, 1430, 900 cm$^{-1}$.

$^1$H NMR (DSMO-d$_6$) δ: 9.15 (s, 0.34H), 9.11 (s, 0.66H), 7.59–7.54 (m, 2H), 7.33–7.30 (m, 2H), 6.39 (s, 0.68H), 6.28 (s, 1.32H), 4.72–4.58 (m, 1H), 4.33–4.25 (m, 0.66H), 4.02–3.96 (m, 0.34H), 3.47–3.35 (m, 1H), 3.25–3.12 (m, 1H), 2.97–2.86 (m, 1H), 1.22–1.12 (m, 7H), 1.04 (d, J=6.96 Hz, 2H).

Example 13

N-(1-[4,5-dihydro-3-(2-naphthyl)isoxazol-5-yl]ethyl)-N-hydroxyurea m.p. 165.3°–166.6° C.

IR (KBr): 3450, 3350, 2850, 1660, 1460, 1170, 810 cm$^{-1}$.

$^1$H NMR (DMSO-d$_6$) δ: 9.19 (s, 1H), 8.11–7.87 (m, 5H), 7.61–7.56 (m, 2H), 6.43 (s, 2H), 4.74–4.64 (m, 1H), 4.11–4.03 (m, 1H), 3.58 (dd, J=10.63, 17.22 Hz, 1H), 3.38 (m, 1H), 1.17 (d, J=6.59 Hz, 3H).

Example 14

N-(1-[4,5-dihydro-3-(3-phenoxyphenyl)isoxazol-5-yl]ethyl)-N-hydroxyurea m.p. 146.4°–147.4° C.

IR (KBr): 3500, 3400, 3150, 1660, 1570, 1440, 1230, 890 cm$^{-1}$.

$^1$H NMR (DSMO-d$_6$) δ: 9.15 (s, 1H), 7.50–7.36 (m, 4H), 7.23–7.05 (m, 5H), 6.41 (s, 2H), 4.64–4.61 (m, 1H), 4.01–3.96 (m, 1H), 3.48–3.42 (m, 1H), 3.15 (dd, J=6.60, 17.22 Hz, 1H), 1.12 (d, J=6.59 Hz, 3H).

Example 15

N-1-(3-[4,5-dihydro-3-(4-fluorophenyl)isoxazol-5-yl]phenyl)ethyl-N-hydroxyurea m.p. 183.7°–185.0° C.

IR (KBr): 3500, 3200, 1650, 1570, 1450, 1230, 900 cm$^{-1}$.

$^1$H NMR (DSMO-d$_6$) δ: 9.07 (s, 1H), 7.80–7.75 (m, 2H), 7.38–7.26 (m, 6H), 6.30 (s, 2H), 5.71 (t, J=8.79 Hz, 1H), 5.31 (dd, J=6.60, 13.92 Hz, 1H), 3.87 (dd, J=10.63, 16.85 Hz, 1H), 3.38 (dd, J=9.16, 17.22 Hz, 1H), 1.40 (d, J=6.96 Hz, 3H).

Example 16

N-[5-(3-tert-butyl-4,5-dihydroisoxazolyl)]methyl-N-hydroxyurea

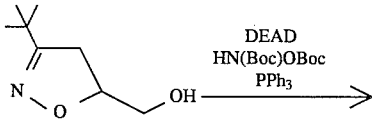

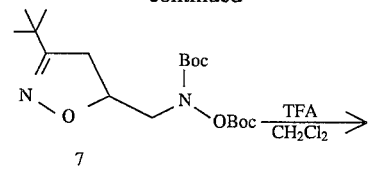

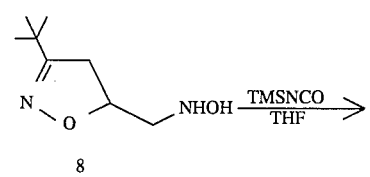

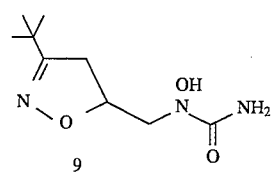

Step 1, 3-tert-butyl-4,5-dihydro-5-hydroxylmethylisoxazole (6)

The title compound (6) was prepared from trimethylacetaldehyde according to the procedures described in Example 1, Step 2.

Step 2, N,O-bis-tert-butoxycarbonyl-N-[5-(3-tert-butyl-4,5-dihydroisoxazolyl)]methylhydroxylamine (7)

To a solution of the product of Step 1, above (6, 10.0 g, 36 mmol), PPh$_3$ (11.3 g, 43 mmol) and N,O-di-tert-butoxycarbonylhydroxylamine (10.1 g, 43 mmol) in THF (100 ml) cooled to −40° C., was added dropwise a solution of diethylazodicarboxylate (7.1 ml, 43 mmol) in THF (10 ml). The reaction mixture was allowed to warm to room temperature over 5 hours and solvent was removed under reduced pressure. The resultant residue was chromatographed on silica gel (eluent=ethyl acetate:n-hexane, 1:4) to afford 14 g (77% yield) of the title compound (7).

$^1$H NMR (CDCl$_3$) δ: 4.77–4.72 (m, 1H), 3.72–3.70 (m, 2H), 3.04 (dd, J=9.52, 16.85 Hz, 1H), 2.92 (dd, J=6.96, 16.85 Hz, 1H), 1.52 (s, 9H), 1.48 (s, 9H), 1.20 (s, 9H).

Step 3, N-[5-(3-tert-butyl-4,5-dihydroisoxazolyl)]methyl-N-hydroxylamine (8)

To a solution of the product of Step 2, above (7, 13.5 g, 26 mmol) in CH$_2$Cl$_2$ (100 ml) cooled to 0° C. was slowly added trifluoroacetic acid (20 ml, 260 mmol). The reaction mixture was allowed to warm to room temperature and was stirred for 2 hours. The reaction mixture was poured carefully into ice cold saturated aqueous NaHCO$_3$ (200 ml), the organic layer was separated and the aqueous layer was extracted with CH$_2$Cl$_2$ (2×200 ml). The combined extracts were washed with water (100 ml), brine (100 ml), dried (MgSO$_4$) and solvent was removed under reduced pressure to give the title compound (8, 4.4 g, 99% yield) as pale yellow solids.

$^1$H NMR (CDCl$_3$) δ: 4.89–4.83 (m, 1H), 4.9–4.45 (br s, 2H), 3.14–3.01 (m, H), 2.73 (dd, J=6.59, 16.85 Hz, 1H), 1.20 (s, 9H).

Step 4, N-[5-(3-tert-butyl-4,5-dihydroisoxazolyl)]methyl-N-hydroxyurea (9)

To a solution of the product of Step 3, above (8, 5.0 g, 29 mmol) in THF (20 ml) was added TMS-NCO (5.7 ml, 43 mmol) and the reaction mixture was stirred at room temperature for 1.5 hours. Methanol (10 ml) was then added and after stirring for 10 minutes, solvent was removed under reduced pressure. The residue was recrystallized from ethyl acetate/isopropyl ether to afford the title compound (9, 2.7 g, 43% yield) as colorless solids, m.p. 107.0°–108.2° C.

IR (KBr): 3500, 3200, 2970, 1690, 1590, 1420, 1180, 880 cm$^{-1}$.

$^1$H NMR (DSMO-d$_6$) δ: 9.46 (s, 1H), 6.33 (s, 2H), 4.70–4.59 (m, 1H), 3.47 (dd, J=6.23, 13.93 Hz, 1H), 3.27 (dd, J=6.59, 13.92 Hz, 1H), 3.04 (dd, J=9.89, 16.85 Hz, 1H), 2.80 (dd, J=6.23, 16.86 Hz, 1H), 1.13 (s, 9H).

Example 17

N-[4,5-dihydro-5-(4-fluorophenyl)isoxazol-3-yl]methyl-N-hydroxyurea

Employing the procedures described in Example 16, above, the title compound was prepared from 4,5-dihydro-5-(4-fluorophenyl)-3-hydroxymethylisoxazole.

m.p. 151.0°–152.5° C.

IR (KBr): 3400, 3240, 1670, 1510, 1230, 1090, 830 cm$^{-1}$.

$^1$H NMR (DSMO-d$_6$) δ: 9.53 (s, 1H), 7.42–7.37 (m, 2H), 7.19 (t, J=9.15 Hz, 2H), 6.53 (s, 2H), 5.55 (dd, J=8.43, 10.99 Hz, 1H), 4.28 (s, 2H), 3.42 (dd, J=10.99, 17.22 Hz, 1H), 2.91 (dd, J=8.43, 17.43 Hz, 1H).

Example 18

N-[4,5-dihydro-3-(4-fluorophenyl)-5-methylisoxazol-4-yl]methyl-N-hydroxyurea

Employing the procedures described in Example 16, above, the title compound was prepared from 4,5-dihydro-3-(4-fluorophenyl)-4-hydroxymethyl-5methylisoxazole.

m.p. 149.2°–150.9° C.

IR (KBr): 3440, 3200, 1660, 1510, 1240, 940 cm$^{-1}$.

$^1$H NMR (DSMO-d$_6$) δ: 9.53 (s, 1H), 7.77–7.71 (m, 2H), 7.34–7.27 (m, 2H), 6.43 (s, 2H), 4.80–4.76 (m, 1H), 3.65–3.61 (m, 1H), 3.49–3.46 (m, 2H), 1.23 (d, J=6.39 Hz, 3H).

Example 19

N-[4,5-dihydro-3-(4-fluorophenyl)-3-methylisoxazol-4-yl]methyl-N-hydroxyurea

Employing the procedures described in Example 16, above, the title compound was prepared from 4,5-dihydro-3-(4-fluorophenyl)-5-hydroxymethyl-4-methylisoxazole.

m.p. 135.4°–137.1° C.

IR (KBr): 3500, 3350, 3150, 2900, 1650, 1570, 1450, 1220, 900, 880 cm$^{-1}$.

$^1$H NMR (DSMO-d$_6$) δ: 9.56 (s, 1H), 7.77–7.72 (m, 2H), 7.31 (t, J=8.79 Hz, 2H), 6.40 (s, 2H), 4.54–4.48 (m, 1H), 3.68–3.64 (m, 1H), 3.52 (dd, J=8.59, 13.92 Hz, 1H), 3.41–3.33 (m, 1H), 1.19 (d, J=6.96 Hz, 3H).

Example 20

N-[4,5-dihydro-3-(4-fluorophenyl)isoxazol-5yl]methyl-N-hydroxyurea

The title compound was prepared according to the procedures described in Example 16, above.

m.p. 171.5°–172.5° C.

IR (KBr): 3450, 3150, 2900, 1650, 1580, 1250, 940 cm$^{-1}$.

$^1$H NMR (DMSO-d$_6$) δ: 9.52 (s, 1H), 7.47–7.69 (m, 2H), 7.33–7.26 (m, 2H), 6.36 (s, 2H), 4.92–4.85 (m, 1H), 3.63 (dd, J=6.60, 14.29 Hz, 1H), 3.49 (dd, J=10.63, 17.22 Hz, 1H), 3.41–3.36 (m, 1H), 3.19 (dd, J=7.32, 16.85 Hz, 1H).

Example 21

N-[4-(3-[4,5-dihydro-3-(4-fluorophenyl)isoxazol-5-yl]phenyl)-3-butyn-2-yl]-N-hydroxyurea

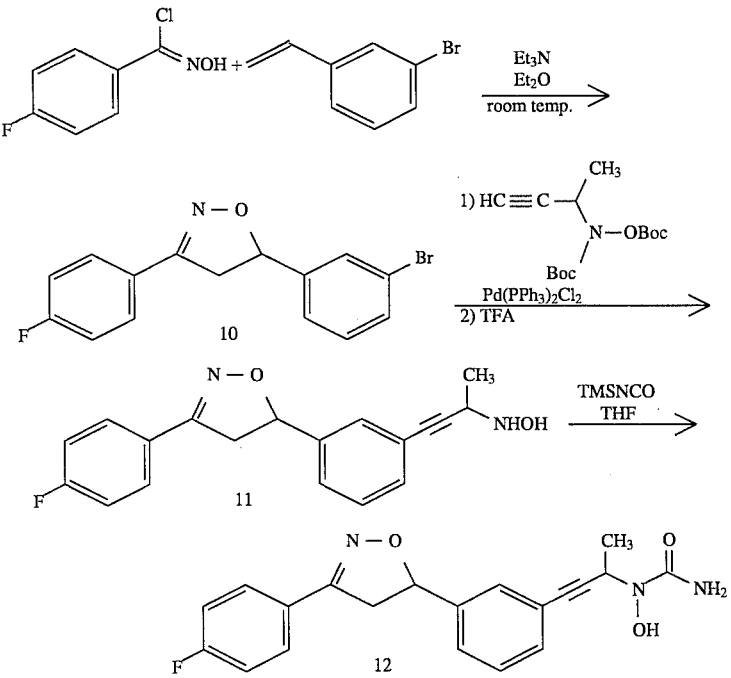

Step 1, 5-(3-bromophenyl)-3-(4-fluorophenyl)-4,5-dihydroisoxazole (10)

A solution of triethylamine (13 ml, 95 mmol) in dry diethyl ether (30 ml) was added dropwise to a solution of 3-bromostyrene (19 g, 104 mmol) and 4-fluorobenzhydroximoyl chloride (15 g, 86 mmol) in diethyl ether (200 ml) at 0° C. The reaction mixture was allowed to warm slowly to ambient temperature and was stirred for 18 hours. Insolubles were removed by filtration and the filtrate was concentrated under reduced pressure. The residue was extracted with ethyl acetate (2×100 ml) and the organic phase was washed with 3N HCl (100 ml), saturated aqueous NaHCO$_3$ (100 ml) and brine (100 ml). The combined extracts were dried over MgSO$_4$ and concentrated under reduced pressure. The residue was chromatographed on silica gel (ethyl acetate:n-hexane=1:7) to give the title compound (10) as pale yellow solids (12 g, 43% yield).

$^1$H NMR (CDCl$_3$) δ: 7.70–7.65 (m, 2H), 7.54 (s, 1H), 7.47–7.43 (m, 1H), 7.33–7.24 (m, 2H), 7.13–7.07 (m, 2H), 5.71 (dd, J=8.06, 10.99 Hz, 1H), 3.78 (dd, J=10.99, 16.49 Hz, 1H), 3.29 (dd, J=8.06, 16.49 Hz, 1H).

Step 2, [4-(3-[4,5-dihydro-3-(4-fluorophenyl)isoxazol-5-yl]phenyl)-3-butyn-2-yl]-hydroxylamine (11)

To a solution of the product of Step 1, above (10, 0.5 g, 1.5 mmol), in triethylamine (4 ml) was added bis(triphenylphosphine)palladium (II) chloride (55 mg, 0.078 mmol) and N,O-bis(tert-butoxycarbonyl)-N-(3-butyn-2-yl)hydroxylamine (840 mg, 2.8 mmol) in triethylamine (1 ml) under a N$_2$ atmosphere. The reaction mixture was stirred at 75° C. for 1.5 hours, then concentrated under reduced pressure. The residue was extracted with ethyl acetate (3×10 ml) and the organic layer was washed with 1N HCl (10 ml), saturated aqueous NaHCO$_3$ (10 ml) and brine (10 ml). The combined extracts were dried over MgSO$_4$ and concentrated under reduced pressure. The residue was chromatographed on silica gel (ethyl acetate:n-hexane=1:6) to give N,O-bis(tert-butoxycarbonyl)-[4-(3-[4,5-dihydro-3-(4-fluorophenyl)isoxazol-5-yl]phenyl)-3-butyn-2-yl]hydroxylamine. To a solution of the protected hydroxylamine thus obtained, in CH$_2$Cl$_2$ (3 ml) cooled to 0° C., was slowly added TFA (0.72 ml, 9.3 mmol). The reaction mixture was allowed to warm to room temperature over 2 hours. The reaction mixture was poured into ice cold saturated aqueous NaHCO$_3$ (20 ml) and extracted with CH$_2$Cl$_2$ (3×15 ml). The combined extracts were washed with water (30 ml) and brine (30 ml) and were dried over MgSO$_4$. After evaporation of solvent, the residue was chromatographed on silica gel (ethyl acetate:n-hexane=1:1) to give the title compound (11, 178 mg, 69% yield) as orange solids.

$^1$H NMR (CDCl$_3$) δ: 7.70–7.64 (m, 2H), 7.24 (s, 1H), 7.41–7.31 (m, 3H), 7.13–7.07 (m, 2H), 5.71 (dd, J=8.06, 10.99 Hz, 1H), 4.13–4.02 (m, 2H), 3.76 (dd, J=10.99, 16.49 Hz, 1H), 3.33 (dd, J=8.06, 16.85 Hz, 1H), 2.17 (d, J=6.67 Hz, 3H).

Step 3, N-[4-(3-[4,5-dihydro-3-(4-fluorophenyl)isoxazol-5-yl]phenyl)-3-butyn-2-yl]-N-hydroxyurea (12)

To a solution of the product of Step 2, above (11, 1.9 g, 5.8 mmol), in THF (10 ml) was added TMS-NCO (1.1 ml, 8.8 mmol), and the reaction mixture was stirred at room temperature for 2 hours. To the mixture was added methanol (5 ml) and the reaction mixture was stirred for 10 minutes and then solvent was removed by evaporation. The residue was chromatographed on silica gel (5% methanol/ethyl acetate) to give the crude title compound. Recrystallization from methanol/n-hexane/ethyl acetate afforded the title compound (12, 1.5 g, 67% yield) as colorless solids.

m.p. 146.0°–147.3° C.

IR (KBr): 3500, 3200, 1660, 1520, 1230, 1160, 900 cm$^{-1}$.

$^1$H NMR (DSMO-d$_6$) δ: 9.33 (s, 1H), 7.87 (dd, J=5.87, 8.80 Hz, 2H), 7.40–7.27 (m, 6H), 6.53 (s, 2H), 5.75 (dd, J=8.42, 10.99 Hz, 1H), 5.12 (q, J=6.96, 13.92 Hz, 1H), 3.88 (dd, J=10.99, 17.22 Hz, 1H), 3.46–3.37 (m, 1H), 1.36 (d, J=6.96 Hz, 3H).

Example 22

N-[4-(3-[4,5-dihydro-5-(4-fluorophenyl)isoxazol-3-yl]phenyl)-3-butyn-2-yl]-N-hydroxyurea Employing the procedures described in Example 21, above, the title compound was prepared from 4-fluorostyrene.

m.p. 131.6°–133.4° C.

IR (KBr): 3500, 3450, 3200, 2900, 1660, 1510, 1250, 1160, 890 cm$^{-1}$.

$^1$H NMR (DSMO-d$_6$) δ: 9.37 (s, 1H), 7.69 (s, 2H), 7.48–7.43 (m, 4H), 7.22 (t, J=9.16 Hz, 2H), 6.56 (s, 2H), 5.76 (t, J=8.79 Hz, 1H), 5.18–5.13 (m, 1H), 3.88 (dd, J=10.99, 17.21 Hz, 1H), 3.49–3.42 (m, 1H), 1.37 (d, J=6.96 Hz, 3H).

Example 23

N-[4-(3-[4,5-dihydro-3-(3-phenoxyphenyl)isoxazol-5-yl]phenyl)-3-butyn-2-yl]-N-hydroxyurea The title compound was prepared employing the procedures described in Example 21, above.

IR (KBr): 3400, 2950, 1570, 1490, 1400, 1220, 910 cm$^{-1}$.

$^1$H NMR (DSMO-d$_6$) δ: 9.35 (s, 1H), 7.48–7.34 (m, 9H), 7.21–7.18 (m, 1H), 7.15–7.05 (m, 3H), 6.55 (s, 2H), 5.75 (dd, J=8.43, 10.99 Hz, 1H), 5.14–5.12 (m, 1H), 3.86 (dd, J=10.99, 17.22 Hz, 1H), 3.45–3.36 (m, 1H), 1.36 (d, J=6.96 Hz, 3H).

Example 24

N-[4-(4-[4,5-dihydro-3-(4-fluorophenyl)isoxazol-5-yl]phenyl)-3-butyn-2-yl]-N-hydroxyurea m.p. 184.7°–185.8° C.

IR (KBr): 3490, 3260, 1660, 1510, 1410, 1220, 840 cm$^{-1}$.

$^1$H NMR (DSMO-d$_6$) δ: 9.35 (s, 1H), 7.79–7.74 (m, 2H), 7.43–7.31 (m, 6H), 6.55 (s, 2H), 5.75 (dd, J=8.43, 10.99 Hz, 1H), 5.13 (dd, J=6.96, 13.92 Hz, 1H), 3.89 (dd, J=19.99, 17.22 Hz, 1H), 3.47–3.41 (m, 1H), 1.36 (d, J=6.96 Hz, 3H).

Example 25

N-[4-(5-[4,5-dihydro-5-(4-fluorophenyl)isoxazol-3-yl]-2-fluorophenyl)-3-butyn-2-yl]-N-hydroxyurea m.p. 85.5°–88.4° C. (amorphous).

IR (KBr): 3500, 3400–3200, 1660, 1510, 1420, 1230, 830 cm$^{-1}$.

$^1$H NMR (CDCl$_3$) δ: 9.38 (s, 1H), 7.77–7.75 (m, 2H), 7.48–7.43 (m, 3H), 7.38–7.35 (m, 2H), 6.58 (s, 2H), 5.76 (t, J=8.79 Hz, 1H), 5.18 (dd, J=6.96, 13.92 Hz, 1H), 3.87 (dd, J=10.99, 17.22 Hz, 1H), 3.45 (dd, J=8.79, 17.59 Hz, 1H), 1.38 (d, J=6.96 Hz, 3H).

Example 26

N-[4-(3-[5-(4-chlorophenyl)-4,5-dihydroisoxazol-3-yl]phenyl)-3-butyn-2-yl]-N-hydroxyurea m.p. 180.9–182.2° C.

IR (KBr): 3470, 3250, 1680, 1650, 1580, 1480, 1340, 1320, 1250, 1090, 890 cm$^{-1}$.

¹H NMR (DMSO-d₆) δ: 9.38 (s, 1H), 7.71–7.68 (m, 2H), 7.47–7.39 (m, 6H), 6.56 (s, 2H), 5.76 (dd, J=8.06, 10.99 Hz, 1H), 5.13 (dd, J=6.59, 13.55 Hz, 1H), 3.88 (dd, J=10.99, 17.22 Hz, 1H), 3.47–3.42 (m, 1H), 1.36 (d, J=6.97 Hz, 3H).

Example 27

N-(4-[3-(4,5-dihydro-5-phenylisoxazol-3-yl)phenyl]-3-butyn-2-yl)-N-hydroxyurea m.p. 151.8°–153.0° C.

IR (KBr): 3400, 3200, 1670, 1570, 1120, 890 cm⁻¹.

¹H NMR (DMSO-d₆) δ: 9.38 (s, 1H), 7.73–7.69 (m, 2H), 7.49–7.32 (m, 7H), 6.56 (s, 2H), 5.74 (dd, J=8.79, 10.99 Hz, 1H), 5.14 (dd, J=6.96, 13.92 Hz, 1H), 3.88 (dd, J=10.99, 17.22 Hz, 1H), 3.47–3.43 (m, 1H), 1.37 (d, J=6.96 Hz, 3H).

Example 28

N-[4-(3-[4,5-dihydro-5-(4-fluorophenyl)isoxazol-3-yl]phenyl)-3-butyn-2-yl]-N'-ethyl-N-hydroxyurea m.p. 129.0°–130.4° C.

IR (KBr): 3400, 3200, 2900, 1630, 1510, 1220, 800 cm⁻¹.

¹H NMR (DMSO-d₆) δ: 9.31 (s, 1H), 7.69–7.67 (m, 2H), 7.46–7.42 (m, 4H), 7.24–7.19 (m, 3H), 5.75 (t, J=8.79 Hz, 1H), 5.11 (dd, J=6.98, 14.29 Hz, 1H), 3.86 (dd, J=10.99, 17.22 Hz, 1H), 3.46–3.38 (m, 1H), 3.13–3.03 (m, 2H), 1.36 (d, J=6.96 Hz, 3H), 1.00 (t, J=7.33 Hz, 3H).

Example 29

N-[4-(4-chloro-3-[4,5-dihydro-5-(4-fluorophenyl)isoxazol-3-yl]phenyl)-3-butyn-2-yl]-N-hydroxyurea m.p. 125.0°–126.3° C.

IR (KBr): 3400, 3200, 1670, 1510, 1480, 1220, 900, 830 cm⁻¹.

¹H NMR (DSMO-d₆) δ: 9.37 (s, 1H), 7.67–7.46 (m, 5H), 7.24–7.21 (m, 2H), 6.58 (s, 2H), 5.78 (dd, J=8.79, 10.99 Hz, 1H), 5.14 (dd, J=6.96, 13.92 Hz, 1H), 3.94 (dd, J=10.99, 17.22 Hz, 1H), 3.46 (dd, J=8.42, 17.22 Hz, 1H), 1.36 (d, J=6.97 Hz, 3H).

Example 30

N-[4-(3-[5-(4-chlorophenyl)-4,5-dihydroisoxazol-3-yl]phenyl)-3-butyn-2-yl]-N-hydroxy-N'-methylurea m.p. 177.6°–179.5° C.

IR (KBr): 3450, 3100–3200, 2900, 1640, 1530, 1490, 820 cm⁻¹.

¹H NMR (DSMO-d₆) δ: 9.30 (s, 1H), 7.72–7.67 (m, 2H), 7.48–7.41 (m, 6H), 7.12–7.11 (m, 1H), 5.77 (dd, J=8.43, 11.46 Hz, 1H), 5.16–5.18 (m, 1H), 3.89 (dd, J=10.99, 17.22 Hz, 1H), 3.44 (dd, J=8.06, 17.22 Hz, 1H), 2.62 (d, J=4.40 Hz, 3H), 1.37 (d, J=6.96 Hz, 3H).

Example 31

N-[3-(3-[4,5-dihydro-5-(4-fluorophenyl)isoxazol-3-yl]phenyl)-2-propyn-1-yl]-N-hydroxyurea m.p. 181.4°–184.0° C. (decomposed).

IR (KBr): 3450, 3200, 1640, 1520, 1250, 900 cm⁻¹.

¹H NMR (DMSO-d₆) δ: 9.63 (s, 1H), 7.74–7.71 (m, 2H), 7.53–7.43 (m, 4H), 7.25–7.19 (m, 2H), 6.58 (s, 2H), 5.76 (dd, J=8.42, 10.62 Hz, 1H), 4.35 (s, 2H), 3.88 (dd, J=10.99, 17.22 Hz, 1H), 3.44 (dd, J=8.43, 17.22 Hz, 1H).

Example 32

N-[3-(3-[4,5-dihydro-5-(4-fluorophenyl)isoxazol-3-yl]phenyl)-2-propyn-1-yl]-N-hydroxy-N'-methylurea m.p. 165.2°–166.4° C.

IR (KBr): 3390, 3250, 1630, 1560, 1520, 1250, 1100, 830 cm⁻¹.

¹H NMR (DMSO-d₆) δ: 9.59 (s, 1H), 7.75–7.71 (m, 2H), 7.52–7.43 (m, 4H), 7.23–7.19 (m, 2H), 7.15–7.10 (m, 1H), 5.76 (dd, J=8.79, 10.99 Hz, 1H), 4.35 (s, 2H), 3.88 (dd, J=10.99, 17.22 Hz, 1H), 3.44 (dd, J=8.80, 17.22 Hz, 1H), 2.62 (d, J=4.77 Hz, 3H).

Example 33

(Z)-N-[3-(3-[4,5-dihydro-5-(4-fluorophenyl)isoxazol-3-yl]phenyl)-2-propen-1-yl]-N-hydroxyurea Step 1, 4,5-dihydro-5-(4-fluorophenyl)-3-(3-iodophenyl)isoxazole (13)

The title compound (13) was prepared from 3-iodobenzaldehyde according to the procedures described in Example 21, Step 1.

¹H NMR (CDCl₃) δ: 8.02 (s, 1H), 7.75 (d, J=8.06 Hz, 1H), 7.66 (d, J=7.69 Hz, 1H), 7.35 (dd, J=5.50, 8.80 Hz, 2H), 7.18–7.03 (m, 3H), 5.74 (dd, J=8.06, 10.99 Hz, 1H), 3.74 (dd, 11.36, 16.86 Hz, 1H), 3.27 (dd, J=8.42, 16.86 Hz, 1H).

Step 2, 3-(3-[4,5-dihydro-5-(4-fluorophenyl)isoxazol-3-yl]phenyl)-2-propyn-1-ol (14)

To a solution of the product of Step 1, above (13, 5.5 g, 15 mmol) in triethylamine (40 ml), was added bis(triphenylphosphine)palladium (II) chloride (0.63 g, 0.9 mmol) and propargyl alcohol (1.4 g, 25 mmol) under a nitrogen atmosphere. After stirring at room temperature for 1 hour, CuI (0.25 g, 1.3 mmol) was added to the reaction mixture. The reaction mixture was stirred at room temperature for 18 hours, insolubles were removed by filtration and the filtrate was concentrated under reduced pressure. The residue was partitioned between ethyl acetate (100 ml) and water (100 ml) and the aqueous layer were separated and extracted with ethyl acetate (100 ml×2). The combined organic layers were washed with aqueous 1N HCl (150 ml), aqueous NaHCO₃ (150 ml) and brine (150 ml), dried (MgSO₄) and concentrated under reduced pressure. The residue was purified by column chromatography on silica gel (eluent=ethyl acetate:n-hexane, 1:4) to give 4.3 g (95% yield) of the title compound (14) as pale yellow solids.

¹H NMR (CDCl₃) δ: 7.72–7.69 (m, 2H), 7.49–7.48 (m, 1H), 7.46–7.33 (m, 3H), 7.09–7.03 (m, 2H), 5.73 (dd, J=8.43, 10.99 Hz, 1H), 4.50 (d, J=5.86 Hz, 2H), 3.75 (dd, J=10.99, 16.49 Hz, 1H), 3.28 (dd, J=8.06, 16.85 Hz, 1H), 1.79 (t, J=5.86 Hz, 1H).

Step 3, (Z)-3-(3-[4,5-dihydro-5-(4-fluorophenyl)isoxazol-3-yl]phenyl)-2-propen-1-ol (15)

A mixture of the product of Step 2, above (14, 2.0 g, 6.8 mmol) and 5% Pd/BaSO₄ (200 mg) in methanol was subjected to hydrogenation at atmospheric pressure. After the absorption of the required amount of hydrogen, the suspension was filtered and washed with methanol. Methanol was evaporated from the filtrate. The residue was purified by column chromatography on silica gel (eluent=ethyl acetate:n-hexane, 1:4) to give 1.8 g (95% yield) of the title compound as pale yellow solids.

$^1$H NMR (CDCl$_3$) δ: 7.56 (d, J=6.60 Hz, 2H), 7.41–7.33 (m, 3H), 7.27–7.25 (m, 1H), 7.05 (t, J=8.79 Hz, 2H), 6.56 (d, J=11.72 Hz, 1H), 5.95 (dd, J=6.60, 11.72 Hz, 1H), 5.71 (t, J=8.42 Hz, 1H), 4.42 (br s, 2H), 3.77 (dd, J=10.99, 16.48 Hz, 1H), 3.29 (dd, J=8.06, 16.85 Hz, 1H), 2.00 (br s, 1H).

Step 4, (Z)-N,O-di-tert-butoxycarbonyl-N-[3-(3-[4,5-dihydro-5-(4-fluorophenyl)isoxazol-3-yl]phenyl)-2-propen-1-yl]-N-hydroxylamine (16)

To a solution of the product of Step 3, above (15, 1.8 g, 6 mmol), PPh$_3$ (1.9 g, 7.2 mmol) and N,O-di-tert-butoxycarbonylhydroxylamine (1.85 g, 7.8 mmol) in THF (25 ml) was added dropwise a solution of diethylazodicarboxylate (1.2 ml, 7.2 mmol) in THF (5 ml) under a nitrogen atmosphere. The reaction mixture was stirred at room temperature for 1.5 hours and solvent was removed under reduced pressure. The resultant residue was purified by column chromatography on silica gel (eluent=ethyl acetate:n-hexane, 1:7) to afford 3.0 g (98% yield) of the title compound (16) as a colorless oil.

1H NMR (CDCl$_3$) δ: 7.63 (d, J=7.69 Hz, 1H), 7.53 (s, 2H), 7.42–7.35 (m, 2H), 7.28 (d, J=9.53 Hz, 1H), 7.11–7.03 (m, 2H), 6.64 (d, J=11.72 Hz, 1H), 5.91–5.81 (m, 1H), 5.73 (dd, J=8.43, 10.99 Hz, 1H), 4.45 (d, J=6.23 Hz, 2H), 3.79 (dd, J=10.99, 16.85 Hz, 1H), 3.32 (dd, J=8.06, 16.85 Hz, 1H), 1.48 (s, 9H), 1.45 (s, 9H).

Step 5, (Z)-N-[3-(3-[4,5-dihydro-5-(4-fluorophenyl)isoxazol-3-yl]phenyl)-2-propen-1-yl]-N-hydroxylamine (17)

To a solution of the product of Step 4, above (16, 3.2 g, 6.2 mmol) in CH$_2$Cl$_2$ (30 ml) cooled to 0° C., was slowly added trimethylsilyl trifluoromethanesulfonate (2.5 ml, 13.4 mmol) under a nitrogen atmosphere. The reaction mixture was allowed to warm to room temperature and was stirred for 1.5 hours. The reaction mixture was poured carefully into ice cold water (30 ml), the organic layer was separated and the aqueous layer was extracted with CH$_2$Cl$_2$ (30 ml×3). The combined extracts were washed with aqueous NaHCO$_3$ (50 ml) and brine (50 ml), then was dried (MgSO$_4$) and solvent was removed under reduced pressure to afford the title compound (17, (1.8 g, 93% yield) as pale yellow solids.

1H NMR (CDCl$_3$) δ: 7.64 (s, 1H), 7.58–7.55 (m, 1H), 7.42–7.32 (m, 4H), 7.09–7.03 (m, 2H), 6.64 (d, J=11.72 Hz, 1H), 5.93–5.83 (m, 1H), 5.73 (dd, J=8.43, 11.00 Hz, 1H), 3.84 (dd, J=1.83, 5.50 Hz, 2H), 3.78 (dd, J=10.99, 16.84 Hz, 1H), 3.30 (dd, J=8.43, 16.85 Hz, 1H).

Step 6, (Z)-N-[3-(3-[4,5-dihydro-5-(4-fluorophenyl)isoxazol-3-yl]phenyl)-2-propen-1-yl]-N-hydroxyurea (18)

To a solution of the product of Step 5, above (17, 0.66 g, 2.1 mmol), in THF (10 ml) was added TMSNCO (0.42 ml, 3.1 mmol) under a nitrogen atmosphere and the reaction mixture was stirred at room temperature for 1 hour. Methanol (5 ml) was then added and after stirring for 10 minutes, solvent was removed under reduced pressure. The residue was recrystallized from ethyl acetate/methanol to afford the title compound (18, 340 mg, 45% yield) as colorless solids.

m.p. 152.0°–153.5° C.

IR (KBr): 3450, 3200, 2900, 1620, 1580, 1520, 1250, 1190, 840 cm$^{-1}$.

$^1$H NMR (DMSO-d$_6$) δ: 9.42 (s, 1H), 7.64 (d, J=6.60 Hz, 2H), 7.49–7.39 (m, 4H), 7.22 (t, J=8.79 Hz, 2H), 6.59 (d, J=11.72 Hz, 1H), 6.41 (s, 1H), 5.88–5.72 (m, 2H), 4.25 (d, J=6.23 Hz, 2H), 3.89 (dd, J=10.99, 17.22 Hz, 1H), 3.42 (dd, J=8.43, 8.22 Hz, 1H).

Example 34

(Z)-N-[3-(3-[4,5-dihydro-5-(4-fluorophenyl)isoxazol-3-yl]phenyl)-2-propen-1-yl]-N-hydroxy-N'-methylurea m.p. 144.1°–146.3° C.

IR (KBr): 3470, 3200, 1620, 1540, 1520, 1250, 1100, 940 cm$^{-1}$.

$^1$H NMR (DSMO-d$_6$) δ: 9.36 (s, 1H), 7.63 (d, J=8.79 Hz, 2H), 7.49–7.39 (m, 4H), 7.22 (t, J=8.79 Hz, 2H), 6.98 (d, J=4.40 Hz, 1H), 6.59 (d, J=11.72 Hz, 1H), 5.86–5.72 (m, 2H), 4.23 (d, J=6.23 Hz, 2H), 3.88 (dd, J=10.99, 17.22 Hz, 1H), 3.45 (dd, J=8.80, 17.22 Hz, 1H), 2.58 (d, J=4.76 Hz, 3H).

Example 35

(E)-N-[3-(3-[4,5-dihydro-5-(4-fluorophenyl)isoxazol-3-yl]phenyl)-2-propen-1-yl]-N-hydroxyurea Step 1, (E)-3-(3-[4,5-dihydro-5-(4-fluorophenyl)isoxazol-3-yl]phenyl)-2-propen-1-ol (19)

The acetylenic alcohol product of Example 33, Step 2 (14, 2.2 g, 7.4 mmol) was dissolved in ether (20 ml) and treated dropwise with a solution of 3.2 ml of sodium bis(2-methoxyethoxy)aluminum hydride (Red-Al, 3.2 ml, 70% in toluene) in toluene (10 ml) under a nitrogen atmosphere. The reaction mixture was refluxed for 2 hours, allowed to cool to room temperature and then a solution of aqueous 1N HCl (50 ml) was carefully added. The mixture was filtered and insolubles washed with ethyl acetate and water. The aqueous phase was extracted with ethyl acetate (30 ml×2). The combined organic phases were washed with aqueous NaHCO$_3$ (100 ml) and brine (100 ml), then were dried (MgSO$_4$) and solvent was removed under reduced pressure. The residue was purified by column chromatography on silica gel (eluent=ethyl acetate:n-hexane, 1:1) to afford 1.7 g (77% yield) of the title compound (19).

$^1$H NMR (CDCL$_3$) δ: 7.72 (s, 1H), 7.56–7.53 (m, 1H), 7.46–7.34 (m, 4H), 7.11–7.03 (m, 2H), 6.64 (d, J=16.21 Hz, 1H), 6.47–7.47 (m, 1H), 5.73 (dd, J=8.06, 16.02 Hz, 1H), 4.34 (d, J=4.76 Hz, 2H), 3.79 (dd, J=10.99, 16.85 Hz, 1H), 3.31 (dd, J=8.96, 16.86 Hz, 1H).

Step 2, (E)-N-[3-(3-[4,5-dihydro-5-(4-fluorophenyl)isoxazol-3-yl]phenyl)-2-propen-1-yl]-N-hydroxyurea (20)

The title compound (20) was prepared from the product of Step 1, above (19) according to the procedures described in Example 33.

m.p. 158.7°–160.3° C.

IR (KBr): 3500, 3000, 2900, 1670, 1620, 1520, 1250, 960, 840 cm$^{-1}$.

$^1$H NMR (DSMO-d$_6$) δ: 9.34 (s, 1H), 7.73 (s, 1H), 7.60 (d, J=7.32 Hz, 1H), 7.53–7.39 (m, 4H), 7.22 (t, J=8.79 Hz, 2H), 6.59 (d, J=16.12 Hz, 1H), 6.40–6.30 (m, 3H), 5.76 (t, J=8.80 Hz, 1H), 4.11 (d, J=5.86 Hz, 2H), 3.89 (dd, J=10.99, 17.22 Hz, 1H), 3.45 (dd, J=8.42, 17.22 Hz, 1H).

Example 36

N-(3-[3-(4,5-dihydro-5-phenylisoxazol-3-yl)phenyl]-2-propyn-1-yl)-N-hydroxyurea m.p. 175.1°–177.9° C.

IR (KBr): 3500, 3000, 2900, 1670, 1620, 1520, 1250, 960, 840 cm$^{-1}$.

$^1$H NMR (DSMO-d$_6$) δ: 9.62 (s, 1H), 7.74–7.72 (m, 2H), 7.52–7.34 (m, 7H), 6.56 (s, 2H), 5.74 (dd, J=8.79, 10.62 Hz, 1H), 4.34 (s, 2H), 3.89 (dd, J=10.99, 17.22 Hz, 1H), 3.43 (dd, J=8.79, 17.22 Hz, 1H).

Example 37

N-(3-[3-(4,5-dihydro-5-phenylisoxazol-3-yl)phenyl]-2-propyn-1-yl)-N-hydroxy-N'-methylurea m.p. 159.2°–160.8° C.

IR (KBr): 3370, 3160, 1630, 1550, 1340, 1260, 1100, 900 cm$^{-1}$.

$^1$H NMR (DSMO-d$_6$) δ: 9.57 (s, 1H), 7.75–7.71 (m, 2H), 7.52–7.33 (m, 7H), 7.11–7.09 (m, 1H), 5.75 (dd, J=8.43, 10.99 Hz, 1H), 4.35 (s, 2H), 3.89 (dd, J=10.99, 17.21 Hz, 1H), 3.43 (dd, J=8.43, 17.22 Hz, 1H), 2.62 (d, J=4.76 Hz, 3H).

We claim:

1. A compound of the following chemical formula:

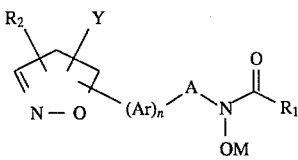

wherein:

R$_1$ is alkyl having 1 to 4 carbon atoms or —NR$_3$R$_4$;

R$_3$ and R$_4$ are each independently hydrogen or alkyl having 1 to 4 carbon atoms;

M is hydrogen or a pharmaceutically acceptable cation;

A is alkylene having 1 to 6 carbon atoms, alkenylene having 2 to 6 carbon atoms or alkynylene having 2 to 6 carbon atoms;

Ar is phenylene or mono-, di- or tri-substituted phenylene wherein the substituents are each independently selected from halogen, alkyl having 1 to 4 carbon atoms and alkoxy having 1 to 4 carbon atoms;

n is an integer of 0 or 1;

Y is hydrogen or alkyl having 1 to 4 carbon atoms;

R$_2$ is alkyl having 1 to 10 carbon atoms, arylalkyl having 1 to 4 carbon atoms in the alkyl moiety, arylalkenyl having 2 to 4 carbon atoms in the alkenyl moiety or aryl; and said aryl and each aryl moiety in said arylalkyl and arylalkenyl are phenyl or naphthyl, and may be substituted by from one to three substituents independently selected from halogen, alkyl having 1 to 6 carbon atoms, alkoxy having 1 to 6 carbon atoms, halosubstituted alkyl having 1 to 4 carbon atoms, halosubstituted alkoxy having 1 to 4 carbon atoms, arylalkoxy having 1 to 4 carbon atoms in the alkoxy moiety, phenoxy and mono-, di- and tri-substituted phenoxy wherein the substituents are each independently selected from halogen, alkyl having 1 to 4 carbon atoms, alkoxy having 1 to 4 carbon atoms and halosubstituted alkyl having 1 to 4 carbon atoms.

2. A compound according to claim 1, wherein:

R$_1$ is NH$_2$;

M is hydrogen; and n is 0.

3. A compound according to claim 2, wherein:

R$_2$ is phenyl or substituted phenyl;

A is —CH$_2$—; and

Y is hydrogen.

4. A compound according to claim 2, wherein:

R$_2$ is phenyl or substituted phenyl;

A is —CH(CH$_3$)—; and

Y is hydrogen.

5. A compound according to claim 4, wherein R$_2$ is phenoxyphenyl or substituted phenoxyphenyl.

6. A compound according to claim 4, wherein R$_2$ is phenoxyphenyl.

7. A compound according to claim 4, wherein R$_2$ is halosubstituted phenyl.

8. A compound according to claim 4, wherein R$_2$ is alkyl substituted phenyl.

9. A compound according to claim 4, wherein R$_2$ is phenyl substituted by halosubstituted alkyl.

10. A compound according to claim 4, wherein R$_2$ is benzyloxyphenyl.

11. A compound according to claim 1, wherein:

R$_1$ is NH$_2$;

M is hydrogen;

Ar is phenylene; and n is 1.

12. A compound according to claim 11, wherein:

R$_2$ is phenyl or substituted phenyl;

A is —CH(CH$_3$)—; and

Y is hydrogen.

13. A compound according to claim 12, wherein R$_2$ is halosubstituted phenyl.

14. A compound according to claim 11, wherein:

R$_2$ is phenyl or substituted phenyl;

A is —C≡CCH(CH$_3$)—; and

Y is hydrogen.

15. A compound according to claim 14, wherein R$_2$ is halosubstituted phenyl.

16. A compound according to claim 15, wherein R$_2$ is fluorophenyl.

17. A compound according to claim 1 selected from:

N-(1-[4,5-dihydro-3-(3-phenoxyphenyl)isoxazol-5-yl]ethyl)-N-hydroxyurea;

N-[1-(3-[4,5-dihydro-3-(4-fluorophenyl)isoxazol-5-yl]phenyl)ethyl]-N-hydroxyurea;

N-[4-(3-[4,5-dihydro-3-(4-fluorophenyl)isoxazol-5-yl]phenyl)-3-butyn- 2-yl]-N-hydroxyurea; and N-(3-[3-(4,5-dihydro-5-phenylisoxazol-3-yl)phenyl]-2-propyn-1-yl)-N-hydroxy-N'-methylurea.

18. A pharmaceutical composition for the treatment of a medical condition for which a 5-lipoxygenase inhibitor is needed, in a mammalian subject, comprising a therapeutically effective amount of a compound according to claim 1 and a pharmaceutically acceptable carrier.

19. A method for the treatment of a medical condition for which a 5-lipoxygenase inhibitor is needed, in a mammalian subject, comprising administering to said subject a therapeutically effective amount of a compound according to claim 1.

* * * * *